United States Patent [19]

Saito et al.

[11] Patent Number: 4,751,019

[45] Date of Patent: Jun. 14, 1988

[54] LIQUID CRYSTAL COMPOUND HAVING METHYLENEOXY GROUP AND COMPOSITION CONTAINING SAME

[75] Inventors: Shinichi Saito; Hiromichi Inoue; Kazutoshi Miyazawa; Takashi Inukai; Kanetsugu Terashima, all of Yokohamashi, Japan

[73] Assignee: Chisso Corporation, Tokyo, Japan

[21] Appl. No.: 1,894

[22] Filed: Jan. 9, 1987

Related U.S. Application Data

[62] Division of Ser. No. 771,585, Sep. 3, 1985, Pat. No. 4,668,427.

[30] Foreign Application Priority Data

Sep. 4, 1984 [JP] Japan ................. 59-185151

[51] Int. Cl.$^4$ .................. G02F 1/13; C09K 19/12; C09K 19/06; C07C 43/20
[52] U.S. Cl. .................. 252/299.66; 252/299.01; 252/299.5; 252/299.6; 252/299.63; 350/350 R; 350/350 S; 568/642; 568/643
[58] Field of Search ........... 252/299.6, 299.66, 299.63, 252/299.01, 299.5; 350/250 R, 250 S; 568/643, 642

[56] References Cited

U.S. PATENT DOCUMENTS

| | | | |
|---|---|---|---|
| 3,025,056 | 4/1977 | Coates et al. | 252/299.66 |
| 4,222,887 | 9/1980 | Matsufuji | 252/299.68 |
| 4,261,651 | 4/1981 | Gray et al. | 252/299.66 |
| 4,357,078 | 11/1982 | Carr et al. | 252/299.63 |
| 4,400,293 | 8/1983 | Romer et al. | 252/299.63 |
| 4,576,732 | 3/1986 | Isogai et al. | 252/299.6 |
| 4,596,667 | 6/1986 | Inukai et al. | 252/299.65 |

FOREIGN PATENT DOCUMENTS

| | | | |
|---|---|---|---|
| 56-138135 | 10/1981 | Japan | 252/299.6 |
| 60-13731 | 1/1985 | Japan | 252/299.6 |

OTHER PUBLICATIONS

Goodby et al., Liquid Crystals Ordered Fluids, vol. 4, 1984, Proceedings of ACS Symposium in U.S.A. in 1982.

Primary Examiner—Teddy S. Gron
Attorney, Agent, or Firm—Wenderoth, Lind & Ponack

[57] ABSTRACT

A novel chiral liquid crystal compound having an optically active group which affords a superior response rate when used as a liquid crystal display element, and a liquid crystal composition containing the same are provided, which chiral liquid crystal compound is expressed by the formula

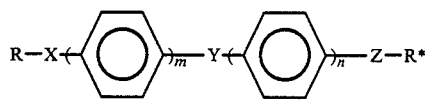

wherein R represents an alkyl group of 1 to 18 carbon atoms; R* represents an optically active alkyl group of 4 to 15 carbon atoms; X represents single bond, —O—,

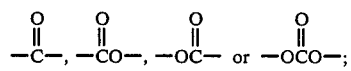

Y represents —CH$_2$O— or —OCH$_2$—; Z represents single bond, —O—,

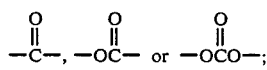

and m and n each represent 1 or 2.

6 Claims, No Drawings

LIQUID CRYSTAL COMPOUND HAVING METHYLENEOXY GROUP AND COMPOSITION CONTAINING SAME

This application is a division of application Ser. No. 771,585, filed Sept. 3, 1985, now U.S. Pat. No. 4,668,427.

BACKGROUND OF THE INVENTION

1. Field of the Invention

This invention relates to a novel liquid crystal substance and a liquid crystal composition containing the same, and more particularly it relates to a chiral liquid crystal substance having an optically active group and a chiral liquid crystal composition containing the same.

2. Description of the Prior Art

Among liquid crystal display elements, those of twisted nematic (TN) type display mode have currently been most widely used, but they are inferior in response rate to emissive type display elements (e.g. electroluminescence, plasma display, etc.), and various improvements in this respect have been attempted, but it appears, nevertheless, that possibility of notable improvement has not been left behind so much. Thus, various liquid crystal display devices based on a different principle from that of TN type display elements have been tried in place thereof. Among these devices, there is a device of display mode utilizing ferroelectric liquid crystals (N. A. Clark et al, Applied Phys. lett., 36, 899 (1980)). This mode utilizes the chiral smectic C phase (hereinafter abbreviated to $S_C^*$ phase), the chiral smectic H phase (hereinafter abbreviated to $S_H^*$ phase) or the like of ferroelectric liquid crystals, and substances having such phases in the vicinity of room temperature have been desired as those suitable to this mode.

The present inventors have previously found some chiral smectic liquid crystal compounds suitable to such object and applied for patent (e.g. Japanese patent application Nos. Sho 58-640/1983, Sho 58-78594/1983, Sho 58-119,590/1983, etc.).

The present inventors have further made extensive research on liquid crystal substances having an optically active group in order to find superior compounds suitable to the above display mode, and as a result have found compounds of the present invention.

SUMMARY OF THE INVENTION

The present invention resides in a compound expressed by the formula

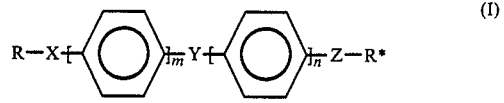

wherein R represents an alkyl group of 1 to 18 carbon atoms; R* represents an optically active alkyl group of 4 to 15 carbon atoms; X represents single bond, —O—,

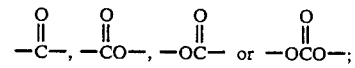

Y represents —CH$_2$O— or —OCH$_2$—; Z represents single bond, —O—,

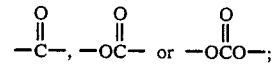

and m and n each represent 1 or 2, and a liquid crystal composition containing the same.

DETAILED DESCRIPTION OF THE PREFERRED EMBODIMENTS

Spontaneous polarization values (Ps) of display elements constituted by the use of the chiral smectic compounds and compositions of the present invention are compared with those of liquid crystal compounds having

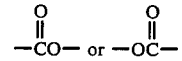

in place of —CH$_2$O— or —OCH$_2$— as Y in the formula (I) expressing the compound of the present invention, recited in Japanese patent applications of the present inventors previously filed (Sho 58-78,594 (1983), Sho 59-119,590 (1984) and Sho 59-142,699 (1984)). As a result, the Ps values of the compounds of the present invention are greater than those of the latter compounds and those of some of the compounds are twice or greater.

Greater Ps values result in various advantages such as lower voltage drive, higher rate responce properties, etc. when display elements are prepared from the compounds. Table 1 shows comparison of Ps values of representatives of the compounds of the present invention expressed by the formula (I), with those of compounds corresponding thereto recited in the patent applications of the present inventors previously filed.

In addition, the Ps values were obtained by measurement at temperatures lower by 10° C. than the upper limit of temperature range exhibiting $S_C^*$ phase.

TABLE 1

| Structural formula | Ps (nC/cm$^2$) | Sample No. |
|---|---|---|
| Compounds of formula (I) | | |

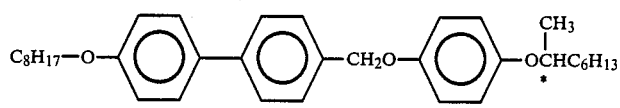

| | 47 | 14 |

TABLE 1-continued

| Structural formula | Ps (nC/cm²) | Sample No. |
|---|---|---|
|  | 80 | 9 |
|  | 105 | 23 |
| Compounds of applications previously filed | | |
| 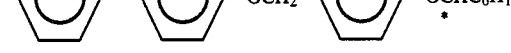<br>(Sho 59-142,699) | 38 | |
| 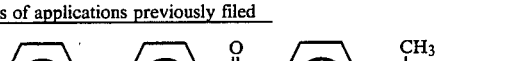<br>(Sho 58-78,594) | 47 | |
| 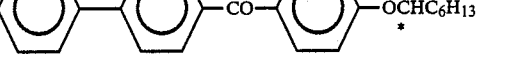<br>(Sho 59-119,590) | 43 | |

In the case of constituting chiral smectic liquid crystal compositions, it is possible to constitute them from a plurality of the compounds of the formula (I), alone, and it is also possible to blend the compound(s) of the formula (I) with other smectic liquid crystals to thereby prepare a liquid crystal composition exhibiting $S_C^*$ phase. Display elements exhibiting the light-switching effect of $S_C^*$ phase have the following three superior specific features as compared with those of TN display mode:

The first specific feature is that the display elements reply at a very high rate so that the response time is 1/100 or less of those of conventional TN mode display elements. The second specific feature is that there is a memory effect so that the multiplex drive is easy in combination thereof with the above high rate response properties. The third specific feature is that when the gray scale is given in the case of TN display mode, this is effected by adjusting the impressed voltage, but there are raised difficult problems such as temperature dependency of threshold voltage, temperature dependency of response rate, etc.; whereas when the light-switching effect of $S_C^*$ phase is applied, it is possible to readily obtain the gray scale by adjusting the reverse time of polarility and hence the display elements are very suitable to graphic display.

As to the display method, the following two may be considered:

One method is of birefringence type using two plates of polarizers and another is of guest-host type using a dichlroic dyestuff. Since $S_C^*$ phase has a spontaneous polarization, the molecule is reversed around the helical axis as a rotating axis by reversing the polarity of impressed voltage. When a liquid crystal composition having $S_C^*$ phase is filled in a liquid crystal display cell subjected to aligning treatment so that the liquid crystal molecules can be aligned in parallel to the electrode surface, followed by placing the liquid crystal cell between two plates of polarizers arranged so that the director of the liquid crystal molecules can be in parallel to the polarization plane on one side, impressing a voltage and reversing the polarity, then a bright field of view and a dark field of view are obtained depending on the opposition angle of the polarizers. On the other hand, in the case of operation by way of the guest-host type, it is possible to obtain a bright field of view and a colored field of view (depending on the arrangement of the polarization plate), by reversing the polarity of impressed voltage.

In addition, compounds of racemic form corresponding to those of the formula (I) are prepared in a similar manner to that in the case of the latter compounds, that is, by using as raw material, compounds of racemic form in place of optically active compounds in the preparation of optically active compounds (I) described below, and the former compounds of racemic form exhibit almost the same phase transition points as those of the latter compounds (I). The compounds of racemic form exhibit $S_C$ phase in place of $S_C^*$ phase, and when they are added to the optically active compounds of formula (I), it is possible to adjust the helical pitch of chiral smectic phases.

Since the compounds of the formula (I) also have an optically active carbon atom, they have a capability of inducing a twisted structure when added to nematic liquid crystals. Nematic liquid crystals having a twisted structure i.e. chiral nematic liquid crystals do not form the so-called reverse domain of TN type display elements; hence it is possible to use the crystals as an inhibitor against reverse domain formation.

Table 2 shows the phase transition points of representatives of the compounds of the formula (I) of the present invention.

TABLE 2

| Sample No. | R | X | m | Y | n | Z | R** | C | S2 | S1 | SC* | SA | I | Remark |
|---|---|---|---|---|---|---|---|---|---|---|---|---|---|---|
| 1 | C6H13 | single bond | 1 | —CH2O— | 2 | single bond | 2-MeBu | .126.5 | — | (SB.124.5) | — | — | . | |
| 2 | C7H15 | single bond | 2 | —OCH2— | 1 | —O— | 1-MeHep | .78.1 | — | — | .101.7 | — | . | Ex. 2 |
| 3 | C8H17 | single bond | 1 | —OCH2— | 2 | single bond | 2-MeBu | .72.5 | SH*.95.3 | SF*.98.2 | .100.7 | .106.0 | . | |
| 4 | C9H19 | single bond | 1 | —OCH2— | 2 | single bond | 2-MeBu | .69.5 | — | SF*.98.8 | .100.8 | .107.0 | . | |
| 5 | C7H15 | —O— | 1 | —CH2O— | 1 | —O— | 2-MeBu | .57.6 | — | (SB.42.1) | (.46.2) | — | . | |
| 6 | C7H15 | —O— | 1 | —CH2O— | 1 | —O— | 1-MeHep | .28.5 | — | — | — | — | . | |
| 7 | C5H11 | —O— | 1 | —CH2O— | 2 | —O— | 1-MeHep | .129.5 | .146.1 | .157.6 | .164.6 | — | . | |
| 8 | C7H15 | —O— | 1 | —CH2O— | 2 | —O— | 2-MeBu | .119 | .127 | .153.0 | .161.6 | — | . | |
| 9 | C7H15 | —O— | 1 | —CH2O— | 2 | —O— | 1-MeHep | .80.1 | — | — | .117.9 | — | . | Ex. 3 |
| 10 | C11H23 | —O— | 1 | —CH2O— | 2 | —O— | 1-MeHep | .90.7 | .100 | — | .114.0 | — | . | |
| 11 | C14H29 | —O— | 1 | —CH2O— | 2 | —O— | 1-MeHep | .93.3 | .96.8 | — | .109.7 | — | . | |
| 12 | C8H17 | —O— | 2 | —CH2O— | 1 | single bond | 1-MeBu | .98.4 | — | .110.6 | .136.7 | .137.4 | . | |
| 13 | C8H17 | —O— | 2 | —CH2O— | 1 | —O— | 2-MeBu | .95 | .107.4 | — | .135.0 | .155.0 | . | |
| 14 | C8H17 | —O— | 2 | —CH2O— | 1 | —O— | 1-MeHep | .63.4 | — | — | .116.0 | — | . | Ex. 1 |
| 15 | C8H17 | —O— | 2 | —CH2O— | 1 | —O— | 4-MeHex | .53.5 | SH*.91.0 | SG*.135.2 | .157.5 | — | . | |
| 16 | C8H17 | —O— | 2 | —CH2O— | 1 | —C(=O)— | 3-MePe | .113.5 | — | — | .147.9 | .158.1 | . | |
| 17 | C8H17 | —O— | 2 | —CH2O— | 1 | —O—C(=O)— | 3-MePe | .52.5 | — | SG*.137.8 | .162.5 | — | . | |
| 18 | C10H21 | —O— | 1 | —OCH2— | 1 | single bond | 2-MeBu | .44.2 | — | — | — | — | . | |
| 19 | C12H25 | —O— | 1 | —OCH2— | 1 | single bond | 2-MeBu | .50.2 | — | — | — | — | . | |
| 20 | C8H17 | —O— | 1 | —OCH2— | 1 | —O— | 1-MeHep | .38 | — | — | — | — | . | |
| 21 | C12H25 | —O— | 1 | —OCH2— | 1 | —O— | 2-MeBu | .54 | — | — | — | — | . | |
| 22 | C8H17 | —O— | 2 | —OCH2— | 1 | —O— | 2-MeBu | .93 | .140.8 | — | .168.3 | — | . | |
| 23 | C9H19 | —O— | 2 | —OCH2— | 1 | —O— | 1-MeHep | .88.3 | .113.0 | — | .128.2 | — | . | |
| 24 | C10H21 | —O— | 2 | —OCH2— | 1 | single bond | 2-MeBu | .85 | SE*.139.1 | SH*.142.3 | .143.5 | — | . | |
| 25 | C8H17 | —O— | 1 | —OCH2— | 2 | —O— | 1-MeHep | .109.0 | — | — | .112.0 | — | . | |
| 26 | C4H9 | —O— | 1 | —OCH2— | 2 | single bond | 2-MeBu | .129.3 | — | — | (.119.5) | (.128.3) | . | |
| 27 | C6H13 | —O— | 1 | —OCH2— | 2 | single bond | 2-MeBu | .112.0 | (SH*.107.1) | (SF*.110.0) | .122.9 | .126.3 | . | |
| 28 | C8H17 | —O— | 1 | —OCH2— | 2 | single bond | 2-MeBu | .106.5 | (SH*.98.0) | SF*.107.9 | .123.4 | .125.0 | . | |
| 29 | C10H21 | —O— | 1 | —OCH2— | 2 | single bond | 2-MeBu | .102.5 | (SH*.98.0) | SF*.105.5 | .120.7 | .122.4 | . | |
| 30 | C12H25 | —O— | 1 | —OCH2— | 2 | single bond | 2-MeBu | .86.0 | — | SF*.104.3 | .117.9 | .120.5 | . | |
| 31 | C8H17 | —C(=O)— | 1 | —OCH2— | 2 | —O— | 1-MeHep | .105.7 | — | — | — | .125.3 | . | |
| 32 | C7H15 | —O—C(=O)— | 1 | —OCH2— | 2 | single bond | 2-MeBu | .77.0 | — | — | — | .86.7 | . | |
| 33 | C8H17 | —O— | 2 | —CH2O— | 1 | —O—C(=O)—O— | 2-MeBu | .56.7 | — | SI*.133.6 | .152.9 | .153.4 | . | |

*: Me represents methyl; Bu, butyl; Hep, heptyl; Hex, hexyl; and Pe, pentyl

In the column of "phase transition point" in Table 2, the symbols "." below the symbols representing the respective phases (C, S2, S1, SC*, SA, I) show that the respective phases are present there, and the symbols "-" show that the respective phases are absent there. Further, a numeral figure on the right side of a symbol "." represents the phase transition point from a phase at the symbol "." to a phase at a symbol "." on the right side of the numeral figure. Further, the symbols "( )" each show monotropic liquid crystal.

Next, preparation of the compounds of the formula (I) will be described.

First, preparation of compounds of formula (Ia) i.e. compounds of formula (I) wherein Y represents —CH2O— will be described.

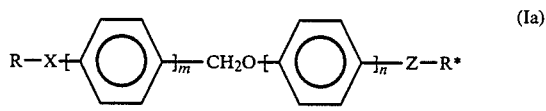
 (Ia)

The compounds of formula (Ia) may be prepared for example as shown in the following figure:

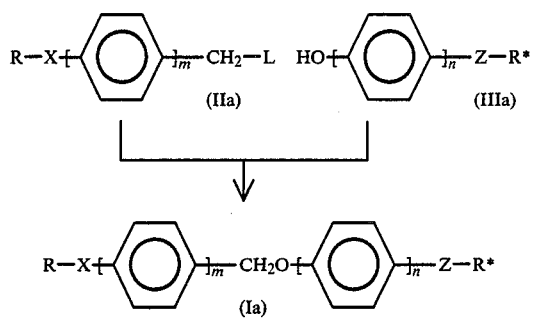

In this figure, R, R*, X, Z, m and n each are as defined above. L represents a group to be eliminated such as halogen atom, tosyloxy group, methylsulfonyloxy group, etc.

Namely, a compound of (IIa) is reacted with a compound (IIIa) in the presence of an alkali in a solvent such as acetone, dimethylformamide (hereinafter abbreviated to DMF), dimethylsulfoxide (hereinafter abbreviated to DMF), dimethylsulfoxide (hereinafter abbreviated to DMSO), etc. to obtain a compound of (Ia).

As the compound of (IIa) as one of the raw materials, the following compounds having either one of the groups indicated as X in formula (I) and a value of 1 or 2 as m therein may be enumerated:

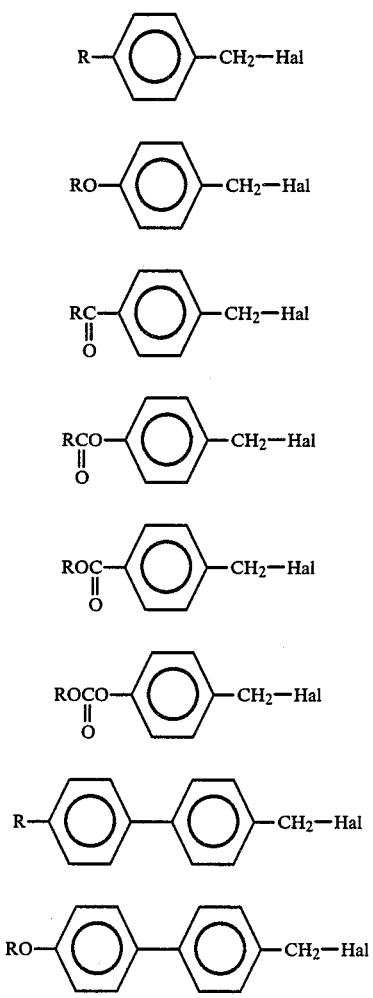

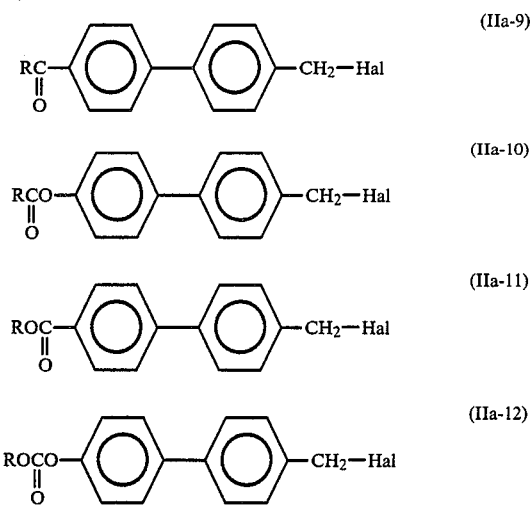

As the compound of (IIIa) as another of the raw materials, the following compounds having either one of the groups indicated as Z in formula (I) and a value of 1 or 2 as n therein may be enumerated:

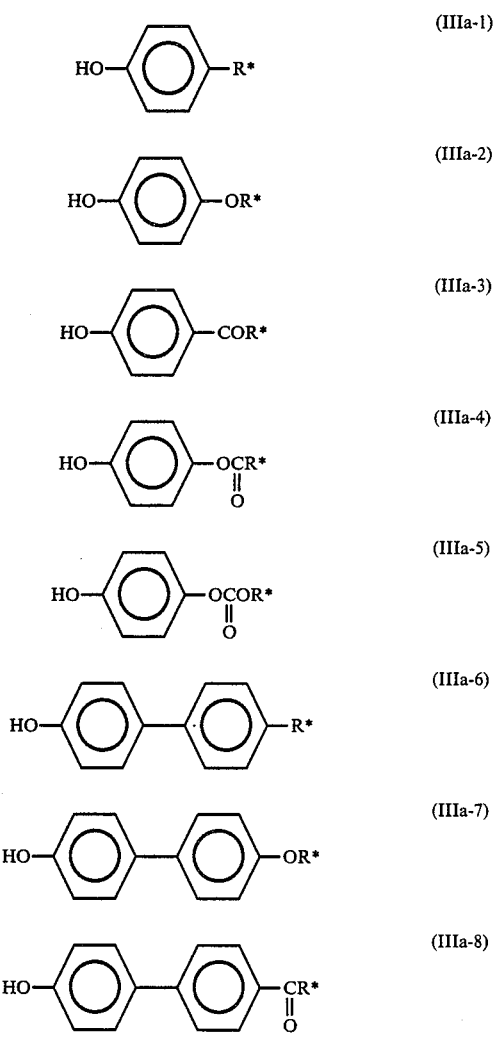

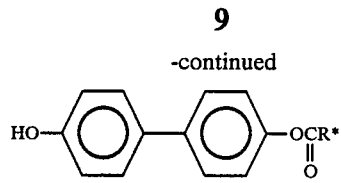 (IIIa-9)

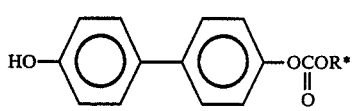 (IIIa-10)

Next, preparation of compounds of formula (Ib), i.e. compounds of formula (I) wherein Y represents —OCH₂— will be described.

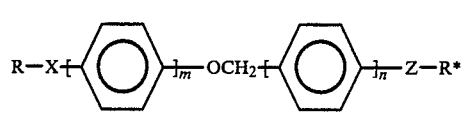 (Ib)

The compounds of formula (Ib) may be prepared for examples as shown in the following figure:

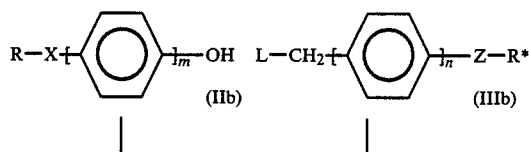

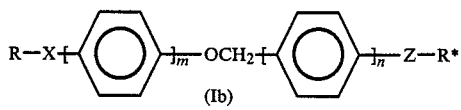

In this figure, R, R*, X, Z, m and n each are as defined above. L represents a group to be eliminated such as halogen atom, tosyloxy group, methylsulfonyloxy group, etc.

Namely, a compound of formula (IIb) is reacted with a compound of formula (IIIb) in the presence of an alkali in a solvent such as acetone, DMF, DMSO, etc. to obtain a compound of formula (Ib).

As the compound (IIb) as one of the raw materials, the following compounds having either one of the groups indicated as X in formula I and a value of 1 or 2 as m therein may be enumerated:

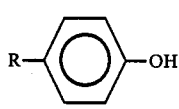 (IIb-1)

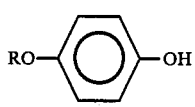 (IIb-2)

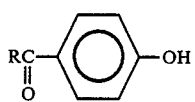 (IIb-3)

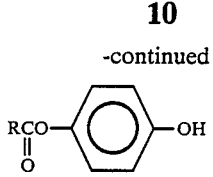 (IIb-4)

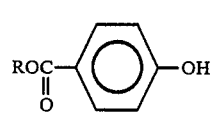 (IIb-5)

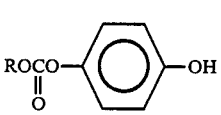 (IIb-6)

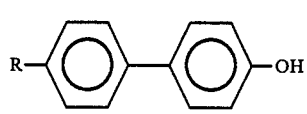 (IIb-7)

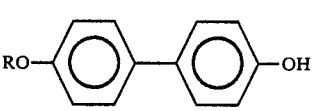 (IIb-8)

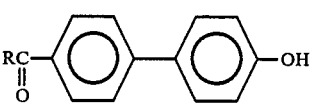 (IIb-9)

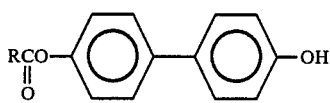 (IIb-10)

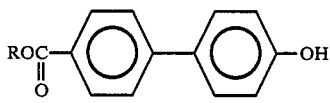 (IIb-11)

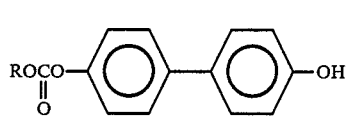 (IIb-12)

As the compound of formula (IIIb) as another of the raw materials, the following compounds having either one of the groups indicated as Z in formula (I) and a value of 1 or 2 as n therein may be enumerated:

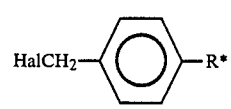 (IIIb-1)

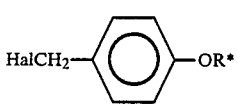 (IIIb-2)

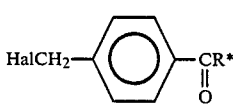 (IIIb-3)

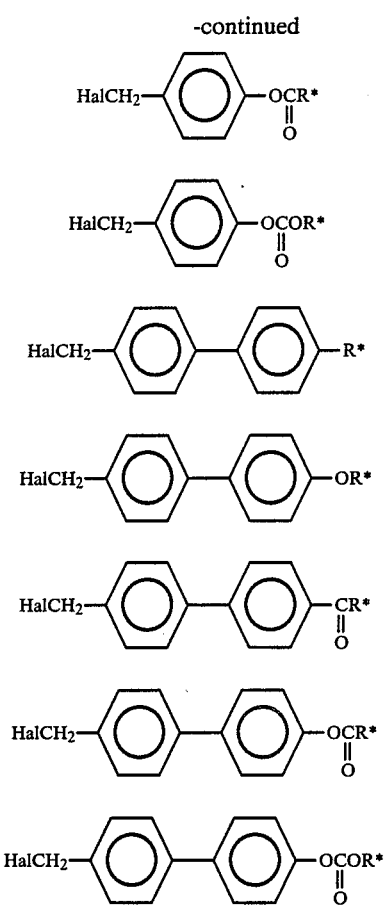

The optically active liquid crystal compounds and liquid crystal compositions of the present invention will be described in more detail by way of Examples.

EXAMPLE 1

Preparation of optically active 4'-octyloxy-4-(p-(1-methylheptyloxy)phenyloxy)methyl-biphenyl (a compound of formula (I) wherein R represents $C_8H_{17}$; $R^*$, 1-methylheptyl; X, —O—; Y, —$CH_2O$—; Z, —O—; m, 2; and n, 1) (No. 14 in Table 1)

(i) Preparation of 4'-octyloxy-4-chloromethyl-biphenyl

4'-Octyloxy-4-formyl-biphenyl (30 g) was suspended in isopropyl alcohol (100 ml), followed by pouring in the resulting suspension, a suspension of sodium boron hydride (1.22 g) in isopropyl alcohol (100 ml), stirring the mixture at 70° C. for 4 hours, adding 6H-HCl (20 ml) and water (10 ml), stirring the mixture at 70° C. for 2 hours, allowing to stand overnight, filtering and collecting the resulting crystals and recrystallizing from ethanol to obtain 4'-octyloxy-4-hydroxymethyl-biphenyl (28.5 g) having a m.p. of 141.6° C. This product (16 g) together with thionyl chloride (12 g) were heated for 6 hours, followed by distilling off excess thionyl chloride and recrystallizing the residue from toluene-heptane to obtain 4'-octyloxy-4-chloromethyl-biphenyl (IIa-8) (14.8 g) having a m.p. of 101° C.

(ii) Preparation of p-(1-methylheptyloxy)phenol p-Benzyloxyphenol (50 g), ethanol (150 ml) and 50% NaOH aqueous solution (25 g) were mixed with stirring, followed by pouring in the mixture, optically active 1-methylheptyl p-toluenesulfonate derived from S-(+)-2-octanol, heating the mixture under reflux for 4 hours, distilling off most of ethanol, extracting with toluene, washing with acid, alkali and water, drying, concentrating and purifying the concentrate according to column chromatography with activated alumina (150 g) to obtain oily p-benzyloxy-(1-methylheptyloxy)benzene (68.6 g), which was then subjected to hydrogenolysis with 5% Pd-C catalyst in ethanol, followed by removing the catalyst, concentrating the solution and subjecting the concentrate to vacuum distillation to obtain oily p-(1-methylheptyloxy)phenol (IIIa-2) (30.7 g) having a b.p. of 129°–130.5° C./0.5 Torr.

(iii) Preparation of the captioned compound

Sodium hydride (0.37 g) was decanted first with heptane, then with THF and placed in a flask in nitrogen stream, followed by dropwise adding a solution of p-(1-methylheptyloxy)phenol (1.5 g) obtained in the above (ii) in THF (20 ml) so that the liquid temperature might not exceed 40° C., then dropwise adding DMSO (20 ml), successively dropwise adding a solution of 4'-octyloxy-4-chloromethyl-biphenyl (1.8 g) obtained in the above (i) in DMSO (40 ml), stirring the mixture at room temperature, allowing to stand overnight, adding 6N-HCl (100 ml), extracting with toluene, washing the toluene layer with acid, washing with alkali, washing with water to make it neutral, drying, concentrating, subjecting the residue to column chromatography with $Al_2O_3$ (10 g), concentrating and twice recrystallizing the concentrate with a mixed solvent of ethanol (20 ml) and ethyl acetate (20 ml) to obtain the, captioned 4'-octyloxy-4-(p-(1-methylheptyloxy)-phenyloxy)methyl-biphenyl (1.8 g). Its phase transition points are described in Table 2 (No. 14). Further its elementary analysis values accorded well with its calculated values as follows:

| | Observed value | Calculated value (in terms of $C_{35}H_{48}O_3$) |
|---|---|---|
| C | 81.1% | 81.35% |
| H | 9.2% | 9.36% |

EXAMPLE 2

Preparation of 4'-heptyl-4-(p-1-methylheptyloxy)phenyl)methyloxy-biphenyl (a compound of formula (I) wherein R represents $C_7H_{15}$; $R^*$, 1-methylheptyl; X, single bond; Y, —$OCH_2$—; Z, —O—; m, 2; and n, 1) (No. 2 in Table 1)

(i) Preparation of p-(1-methylheptyloxy)benzyl chloride p-Hydroxy-benzaldehyde (15 g), ethanol (200 ml) and 50% NaOH (12 g) were mixed with stirring, followed by pouring in the mixture, a tosylate (26 g) derived from S-(+)-2-octanol, heating the resulting mixture under reflux for 6 hours, distilling off most of ethanol, adding 6N-HCl (100 ml), extracting with toluene, washing the toluene layer with acid, washing with alkali, washing with water to make it neutral, drying, concentrating, and further concentrating the resulting concentrate according to column chromatography with $Al_2O_3$ (40 g) to obtain oily p-(1-methylheptyloxy)benzaldehyde (13.0 g). Next, sodium boron hydride (1.0 g) was suspended in isopropyl alcohol (50 ml), followed by dropwise adding to the suspension, a solution of p-(1-methylheptyloxy)benzaldehyde obtained above in isopropyl alcohol (100 ml) so that the liquid temperature might not exceed 40° C., stirring the mixture at 60° C. for 4 hours, adding 6N-HCl (30 ml) and water (20 ml), further heating with stirring at 60° C., distilling off the solvent, extracting the residue with toluene, washing the toluene layer with acid, washing with alkali, washing with water to make it neutral, drying and concentrating to obtain raw p-(1-methylheptyloxy)benzyl alcohol (13 g), which was then heated together with thionyl chloride for 6 hours, followed by distilling off excess thionyl chloride under reduced pressure to obtain raw p-(1-methylheptyloxy)benzyl chloride (IIIb-2) (13 g), which was used, as it was, in the following reaction.

(ii) Preparation of the captioned compound

Sodium hydride (0.21 g) was decanted with n-heptane (20 ml), successively with THF (20 ml) and placed in a flask in nitrogen stream, followed by dropwise adding a solution of 4'-heptyl-4-hydroxy-biphenyl (IIIa-6) (1.18 g) in THF (10 ml), adding DMSO (20 ml) to form a uniform solution. To this solution was dropwise added a solution of p-(1-methyloxy)benzyl chloride (1.05 g) obtained in the above (i) in DMSO (20 ml), followed by stirring the mixture at room temperature, allowing to stand overnight, adding 6N-HCl (100 ml), extracting with toluene, washing the toluene layer with acid, washing with alkali, washing with water to make it neutral, drying, concentrating, subjecting the residue to column chromatography with activated alumina (10 g) to effect separation-concentration using toluene as an elute, and twice recrystallizing from a mixed solvent of ethanol (20 ml) and ethyl acetate (20 ml) to obtain the captioned 4'-heptyl-4-(p-(1-methylheptyloxy)phenyl)-methyloxy-biphenyl (0.6 g). Its phase transition points are described in Table 2 (No. 2).

Further its elementary analysis values accorded well with its calculated values as follows:

|   | Observed value | Calculated value (in terms of $C_{34}H_{46}O_2$) |
|---|---|---|
| C | 84.1% | 83.90% |
| H | 9.3% | 9.53% |

EXAMPLE 3

Preparation of 4'-(p-heptyloxy)phenylmethyloxy)-4-(1-methylheptyloxy)-biphenyl (a compound of formula (I) wherein R represents $C_7H_{15}$; R*, 1-methylheptyl; X, —O—; Y, —CH$_2$O—; m, 1 and; n, 2) (No. 9 in Table 1)

(i) Preparation of p-heptyloxybenzyl bromide

A suspension of sodium boron hydride (6.9 g) in isopropyl alcohol (500 ml) was dropwise added to a solution of p-heptyloxybenzaldehyde (119 g) in isopropyl alcohol (300 ml), followed by heating the mixture to 70° C. to form a uniform solution, which was then agitated at 70° C. for 3 hours and allowed to stand overnight, followed by adding 6N-HCl (100 ml) and water (200 ml), heating the mixture to 60° C., distilling off most of the solvent, extracting with toluene, washing with water, washing with alkali, washing with water to make it neutral, drying, concentrating and recrystallizing the residue from a mixed solvent of ethanol (200 ml) and water (60 ml) to obtain p-heptyloxybenzyl alcohol (74.9 g). This product (40 g) together with 47% aqueous hydrogen bromic acid (200 g) were agitated at 80° C. for 7 hours and allowed to stand overnight, followed by extracting with n-heptane (200 ml), washing the n-heptane layer with water till the washing water became neutral, drying, concentrating and subjecting the residue to vacuum distillation to obtain p-heptyloxybenzyl bromide (IIa-2) (28 g) having a b.p. of 174°–175° C./6 Torr.

(ii) Preparation of the captioned compound

Sodium hydride (0.8 g) was decanted twice with n-heptane (20 ml), successively with THF (20 ml) and placed in a flask in the form of a suspension in THF (20 ml), followed by dropwise adding a solution of 4'-hydroxy-4-(1-methylheptyloxy)-biphenyl (IIIa-7) of m.p. 98.1° C. (5.1 g) obtained by reacting 4,4'-dihydroxybiphenyl with a tosylate derived from S-(+)-2-octanol, in THF (30 ml), thereafter dropwise adding DMSO (20 ml), successively dropwise adding a solution of p-heptyloxybenzyl bromide (5.4 g) in DMSO (30 ml), stirring the mixture at room temperature, allowing to stand overnight, adding 6N-HCl (200 ml), extracting with toluene, washing with acid, washing with alkali, washing with water to make it neutral, drying, concentrating, subjecting the concentrate to column chromatography with activated alumina (20 g) to effect separation-concentration using toluene as an elute, and twice recrystallizing from a mixed solvent of ethanol (40 ml) and ethyl acetate (20 ml) to obtain the captioned 4'-(p-(heptyloxy)phenylmethyloxy)-4-(1-methylheptyloxy)-biphenyl (3.6 g). Its m.p., etc. are described in Table 2. Further its elementary analysis values accorded well with its calculated values as follows:

|   | Observed value | Calculated values (in terms of $C_{34}H_{45}O_3$) |
|---|---|---|
| C | 81.4% | 81.23% |
| H | 9.1% | 9.22% |

EXAMPLE 4 (USE EXAMPLE 1)

A nematic liquid crystal composition consisting of

| 4-ethyl-4'-cyanobiphenyl | 20%, |
|---|---|
| 4-pentyl-4'-cyanobiphenyl | 40%, |
| 4-octyloxy-4'-cyanobiphenyl | 25%, and |
| 4-pentyl-4'-cyanoterphenyl | 15%, | was filled in a cell (distance between electrodes: 10 μm) composed of transparent electrodes subjected to parallel aligning treatment by applying polyvinyl alcohol (PVA) and rubbing the resulting surface to form a TN type display cell, which was observed by a polarizing microscope. As a result, formation of a reverse twist domain was observed.

To the above nematic liquid crystal composition was added a compound of formula (I) of the present invention wherein m represents 1; n, 2; R, $C_6H_{13}$; X, single bond; Y, —CH$_2$O—; Z, single bond; and R*, 2-methylbutyl (No. 1 in Table 2) in a quantity of 0.1% by weight, to observe the mixture in the same TN type cell as above. As a result the reverse twist domain was dissolved and a uniform nematic phase was observed.

EXAMPLE 5 (USE EXAMPLE 2)

A liquid crystal composition consisting of the following compounds of the present invention:

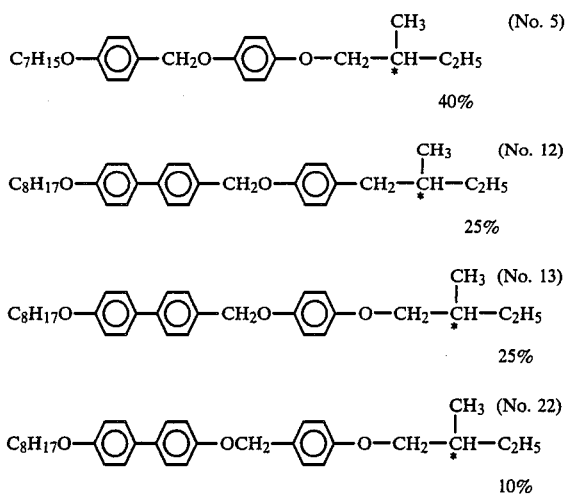

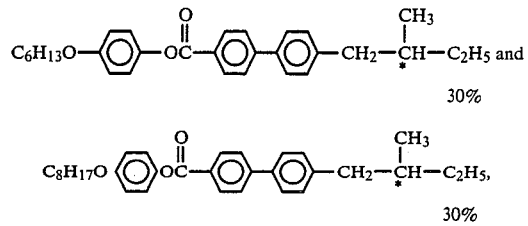

exhibits $S_C^*$ phase in a range of from 50° C. to 95° C., exhibits Ch phase at higher temperatures than the above and forms an isotropic liquid at 142° C.

This blend has a tilt angle as large as 42° at 55° C., and hence it is very suitable to the so-called guest-host type display elements using dichroic dyestuffs, and yet it exhibited as large a spontaneous polarization value as 44 nC/cm².

To this blend was added an anthraquinone dyestuff (D-16, tradename of product made by BDH Company) in a quantity of 3% by weight to prepare a guest-host type liquid crystal composition, which was filled in the same cell as in Example 5 (but cell thickness: 10 μm), and one plate of polarizer was arranged so that its polarization plane might be in parallel to the axis of molecules and an alternate current of a low frequency of 0.5 Hz and 15 V was impressed. As a result, a clear switching operation was observed and there was obtained a color liquid crystal display element having a very good contrast and yet a response rate as very fast as 0.5 m sec at 55° C.

exhibits $S_C^*$ phase in a broad temperature range of from 45° C. to 98° C., exhibits $S_A$-phase at higher temperatures than the above, and forms an isotropic liquid at 107° C.

This blend exhibits a spontaneous polarization value as large as 12 nC/cm² at 50° C. and yet its tilt angle is 22°; hence it is optimum for birefringence type display elements using two polarizing plates.

This blend was filled in a cell of 2 μm thick equipped with transparent electrodes subjected to parallel aligning treatment by applying PVA and rubbing the surface. The resulting liquid crystal cell was placed between two plates of polarizers arranged in a crossed state, and an alternating current of a low frequency of 0.5 Hz and 15 V was impressed. As a result, a clear switching operation having a good contrast was observed, and yet the resulting liquid crystal display element had a response rate as fast as 0.8 m sec at 50° C.

EXAMPLE 6 (USE EXAMPLE 3)

A liquid crystal composition consisting of as compounds of the present invention,

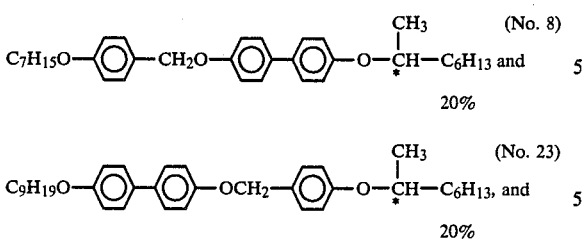

as known, ferroelectric compounds having a small spontaneous polarization value (about 1 nC/cm²) and yet having a large tilt angle of 45°,

What we claim is:

1. A compound of the formula

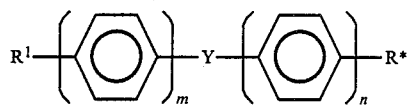

wherein $R^1$ represents an alkyl or alkoxy group of 1 to 18 carbon atoms; $R^*$ represents an optically active alkyl group of 4 to 15 carbon atoms; Y represents —CH₂O— or —OCH₂—; and m and n each represents 1 or 2 but the total of m plus n is 3.

2. A compound according to claim 1 wherein $R^*$ is an optically active alkyl group having one methyl group as its side chain.

3. A compound according to claim 1 wherein $R^*$ is the optically active 2-methylbutyl group.

4. A chiral smectic liquid crystal composition having at least two components at least one of which is a compound set forth in claim 1.

5. A chiral smectic liquid crystal composition consisting of at least two members selected from compounds of the formula of claim 1.

6. A light switching element employing a chiral smectic liquid crystal composition according to claim 4 as a liquid crystal material.

* * * * *